United States Patent [19]

Umezawa et al.

[11] Patent Number: 5,559,115
[45] Date of Patent: Sep. 24, 1996

[54] ONCOGENE FUNCTION-INHIBITORY AGENT, METHOD FOR INHIBITING ONCOGENE FUNCTION, AND TREATMENT OF CANCER

[75] Inventors: Kazuo Umezawa, 1-2-505, Hiroo 3-chome, Shibuya-ku, Tokyo; Takashi Koyano, Kanagawa; Hiroaki Takahashi, Kanagawa; Takashi Yamamoto, Kanagawa, all of Japan

[73] Assignees: Terumo Kabushiki Kaisha; Kazuo Umezawa, both of Tokyo, Japan

[21] Appl. No.: 364,305

[22] Filed: Dec. 27, 1994

[30] Foreign Application Priority Data

Dec. 28, 1993 [JP] Japan .................................. 5-334563

[51] Int. Cl.$^6$ .................................................. A61K 31/44
[52] U.S. Cl. .................................................. 514/279
[58] Field of Search .................................................. 514/279

[56] References Cited

PUBLICATIONS

N. Shimasa et al, The Journal of Antibiotics 34, pp. 1216–1218, Sep. 1981.
O. Itoh et al, Cancer Research 49, pp. 996–1000, Feb. 15, 1989.
Toh Seok Kam et al, Journal of Natural Products, vol. 56, No. 11, pp. 1865–1871, Nov. 1993.
N. Matsuda et al, Cellular Pharmacology I, pp. 219–223, 1994.
Int. J. Cancer, vol. 54, 1993, pp. 450–455, G. J. Peters et al, "Transformation of mouse fibroblasts with the oncogenes H–ras or trk is associated with pronounced changes in drug sensitivity and metabolism."Tetrahedron Lett., vol. 33, No. 7, 1992, pp. 969–972, T. S. Kam et al., "New alkaloid from the leaves of *Tabernaemontana divaricata*".

Phytochemistry, vol. 19, 1980, pp. 1213–1218, S. P. Gunasekera et al, "Anticancer indole alkaloids of *Ervatamia heyneana*".

Primary Examiner—Jerome D. Goldberg
Attorney, Agent, or Firm—Burns, Doane, Swecker & Mathis, L.L.P.

[57] ABSTRACT

A compound isolated from *Ervatamia microphylla* has been found to be effective in inducing a change in cell morphology and growth habits of cultured transformant cell lines, and in reducing the tumor size in a living mammal. The compound is capable of inhibiting the function of oncogenes such as ras and src by inhibiting the function of the oncogene products. The compound is found to be represented by formula (I):

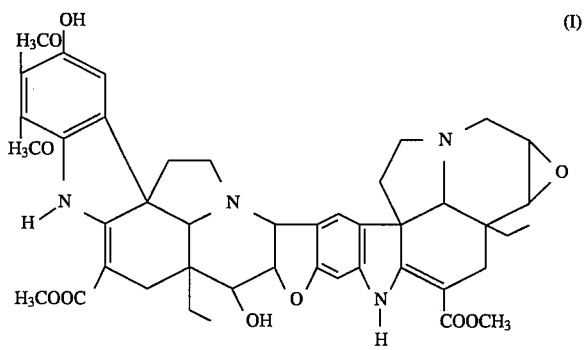

Use of the compound as an oncogene function inhibitor, in a treatment of cancer, and in inducing changes in cell morphology and growth habits in transformant cell line are contemplated.

13 Claims, 12 Drawing Sheets

ONCOGENE FUNCTION-INHIBITORY AGENT, METHOD FOR INHIBITING ONCOGENE FUNCTION, AND TREATMENT OF CANCER

BACKGROUND OF THE INVENTION

1. Field of the Invention

This invention relates to a carcinostatic containing a compound having an activity to inhibit the function of an oncogene as an effective component. More specifically, this invention is directed to a carcinostatic agent which is capable of inhibiting the function of ras and src oncogenes through inhibition of the function of the oncogene products thereof. This invention also relates to a method for inhibiting such oncogene function and a method for normalizing cell morphology and growth habits of cancer cells. Furthermore, this invention relates to a method for treating a cancer of a mammal. This invention involves use of a compound extracted from *Ervatamia microphylla*.

2. Prior Art

Oncogenes play important roles in the initiation and promotion of cancers. An oncogenes is generated by conversion of a protooncogene on a genome DNA of a normal cell through various abnormalities such as point mutation, translocation, and amplification. Of the more than 70 oncogenes that have so far been found, ras oncogenes are some of the most popular oncogenes, and are said to be found in about 20% of human tissues of colon cancer, breast cancer, leukemia, and the like. In view of such situation, substances that are capable of inhibiting the action of the ras and other oncogenes, namely, that are capable of inhibiting the function of the product of ras and other oncogenes is highly awaited as a new series of therapeutic agents. The presently known substances that are capable of inhibiting the action of the ras oncogene product, namely, Ras protein include oxanosin isolated from Actynomyces (N. Shimada et al., The Journal of Antibiotics 34, 1216–1218, 1981) and compactin isolated from a mold (O. Ito et al., Cancer Research 49, 996–1000, 1989).

Such known substances capable of inhibiting the action of the ras oncogene products, however, suffer from low stability and high toxicity, and none are clinically applicable. Development of a new medicament that is clinically applicable, and that has an inhibitory mechanism different from such known oncogene inhibitors is highly demanded.

In order to find an oncogene inhibitory substance of clinical utility, the inventors of the present invention have conducted a screening of substances of plant origin in search for a substance that is capable of inhibiting the action of ras and other oncogenes by using normalization of cell morphology and growth habits for the index, and consequently, found that such an activity is present in an extract of leaves of a tropical plant, *Ervatamia microphylla* Kerr. The inventors of the present invention then succeeded in the isolation and characterization of the active component in the extract. The present invention has been completed on the bases of such study.

SUMMARY OF THE INVENTION

According to the present invention, there is provided an oncogene function-inhibitory agent containing as its effective component a compound represented by formula (I):

which may additionally contain desired pharmaceutically acceptable additives such as a carrier.

According to the present invention, there is also provided a method for inhibiting an oncogene function by using the compound represented by formula (I) wherein the oncogene function is inhibited by inhibiting the function of the oncogene product.

According to the present invention, there is also provided a method for inducing changes in cell morphology and growth habits of cancer cells from those of cancer cells into those of normal cells by using the compound represented by formula (I).

According to the present invention, there is also provided a method for treating a cancer of a mammal wherein the compound represented by formula (I) is administered to the mammal.

In the preferred embodiment of the present invention, the function of at least one member selected from the group consisting of ras oncogenes and src oncogenes is inhibited by the compound of formula (I) through inhibition of the product of such oncogene.

Preferably, the target oncogene whose function is inhibited is a ras gene selected from K, H, and N ras gene, and the target oncogene product whose function is inhibited is a Ras protein.

The compound represented by formula (I) may be the one isolated from *Ervatamia microphylla*.

DETAILED DESCRIPTION OF THE INVENTION

The oncogene inhibitory substance used in the present invention is a substance with a molecular weight of 794 that has been isolated from a tropical plant, *Ervatamia microphylla* Kerr. This substance is hereinafter referred to as III-121C.

Figure 1A:
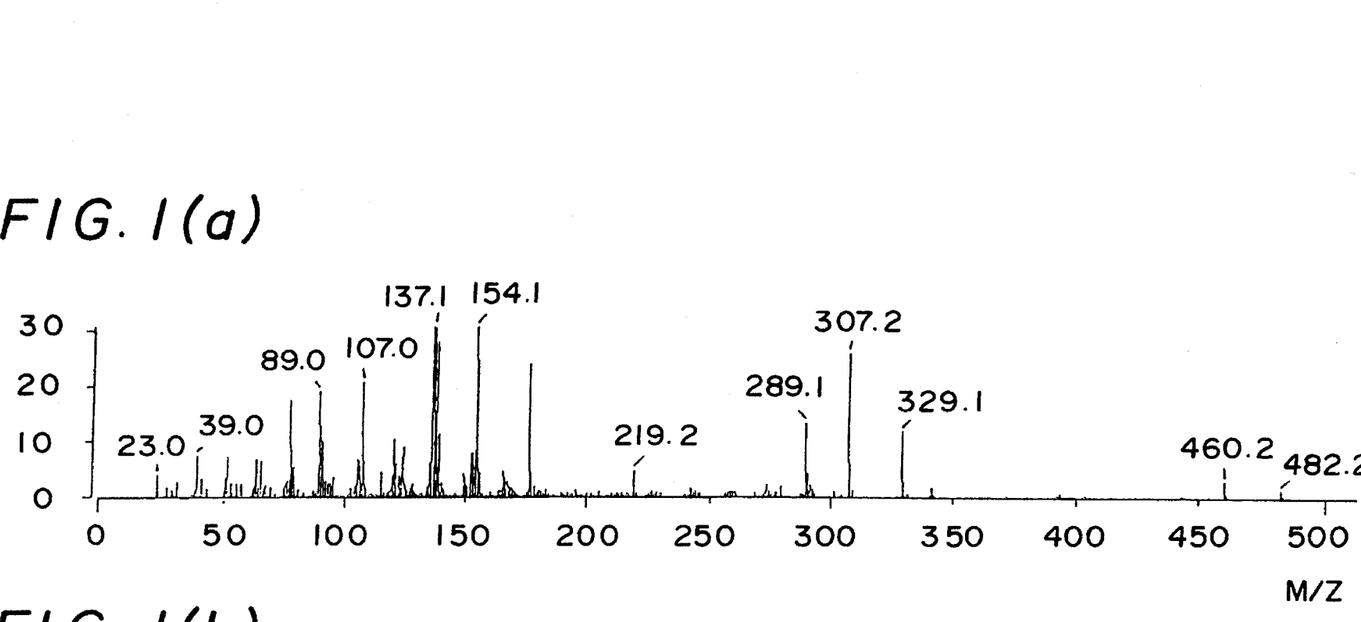
FIG. 1 is a positive spectrum obtained in fast atom bombardment (FAB) mass spectroscopic measurement of III-121C.
Figure 1B:
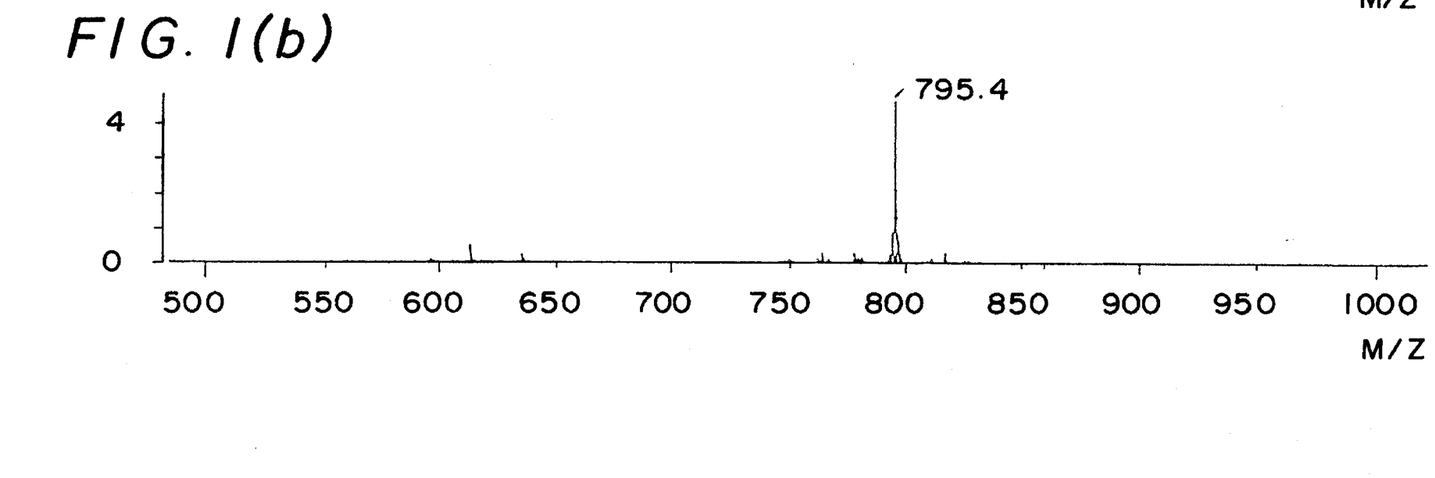
Figure 2A:
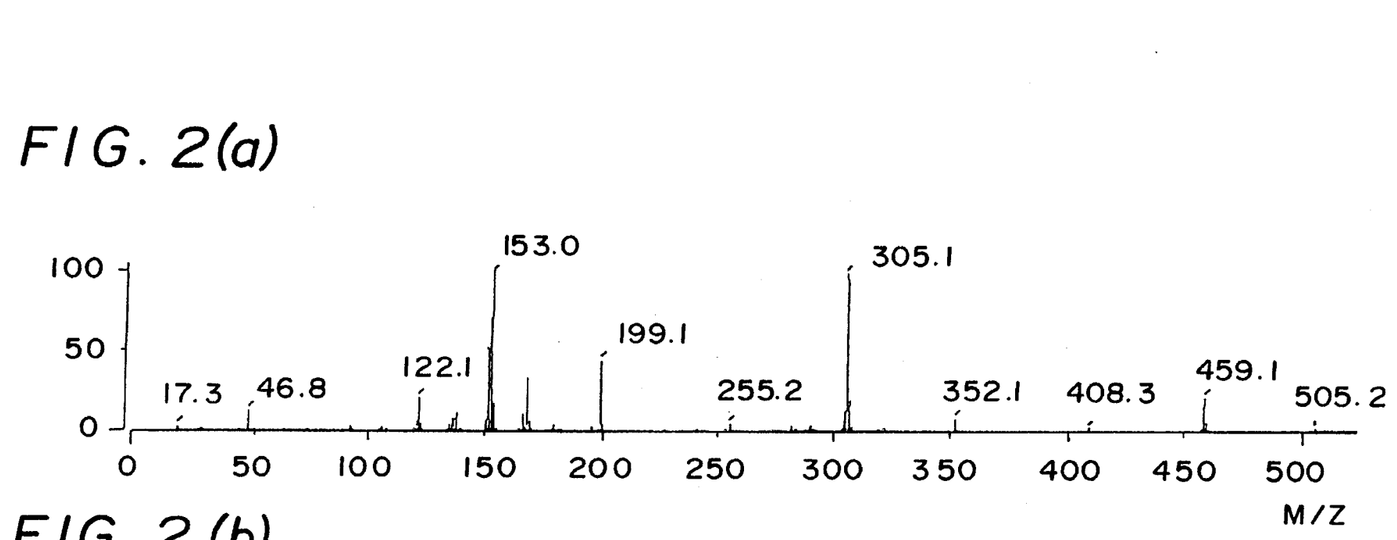
FIG. 2 is a negative spectrum obtained in FAB mass spectroscopic measurement of III-121C.
Figure 2B:
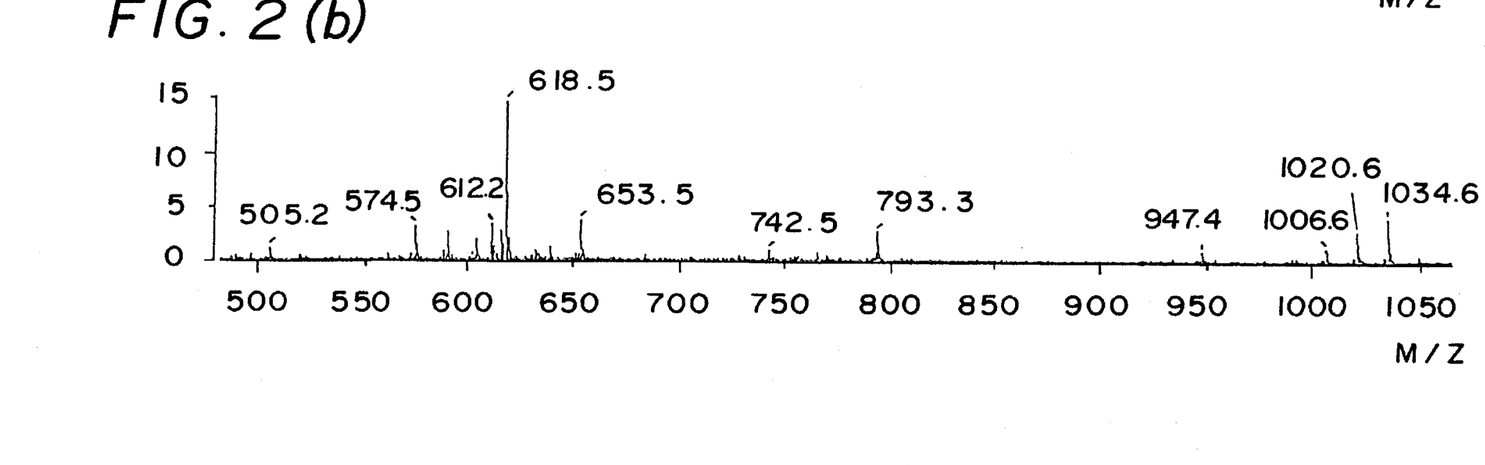

III-121C is a light yellow powdery substance. When this substance was subjected to silica gel thin layer chromatography using developers of 20:1 chloroform:methanol, 1:2 hexane:ethyl acetate, and 2:1 toluene:acetone, respectively, it exhibited an Rf value of 0.56, 0.25, and 0.52. The molecular weight of III-121C was determined by FAB mass spectroscopy to be 794. The positive and negative spectra of the FAB mass spectroscopy are shown in FIGS. 1 and 2, respectively.

Figure 3:
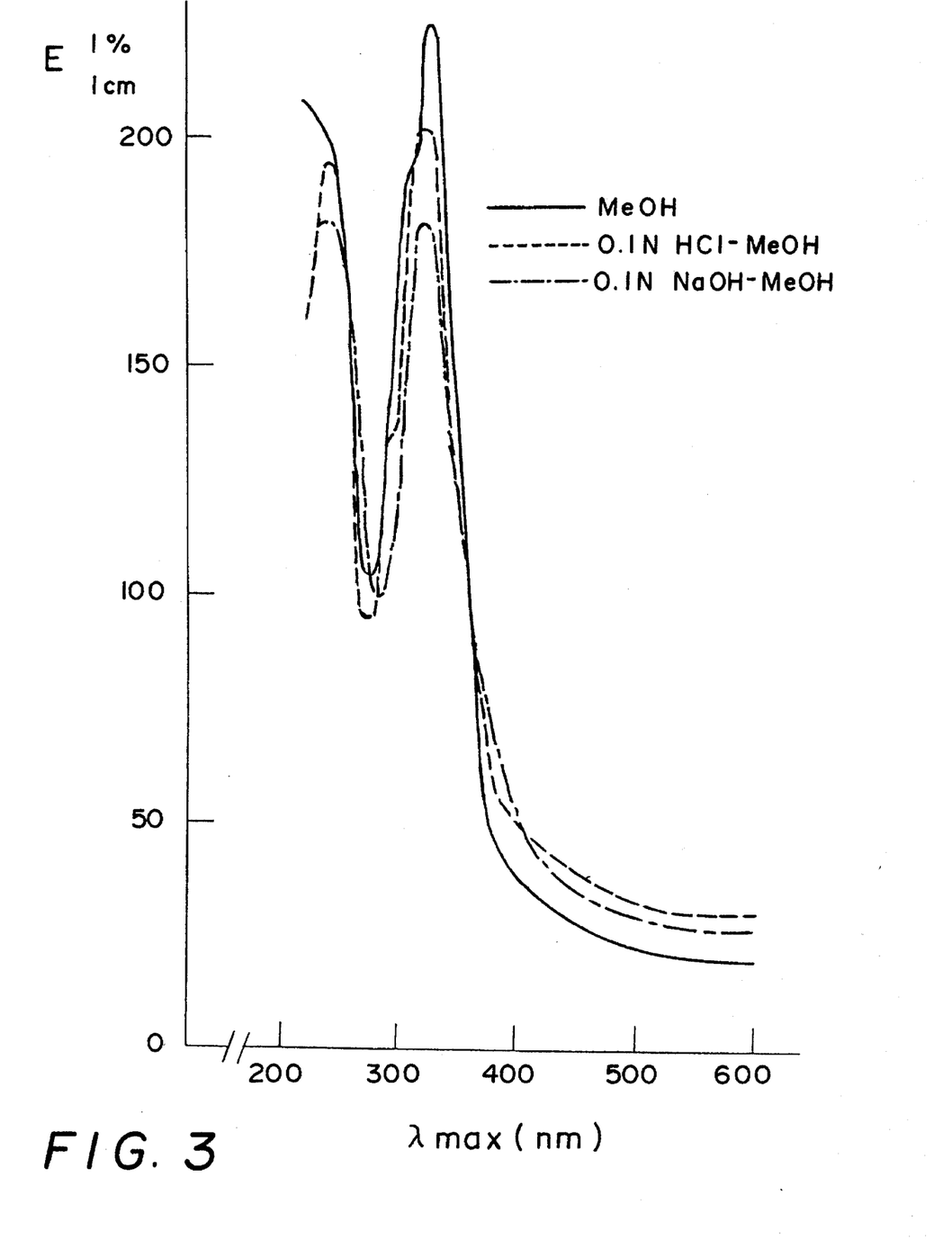
FIG. 3 is a ultraviolet absorption spectrum, λmax (E 1%/1 cm) of III-121C.
Figure 4:
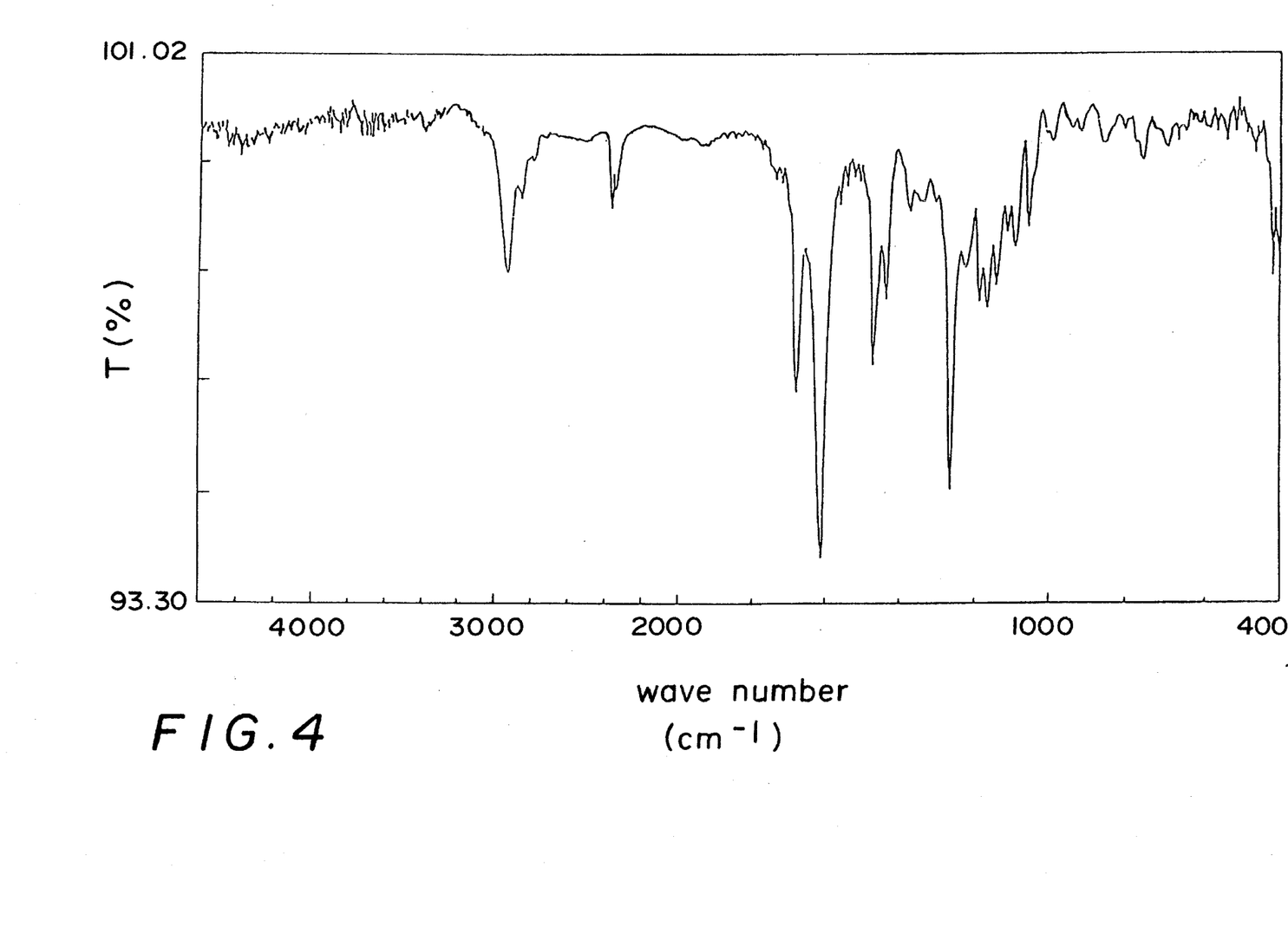
FIG. 4 is an infrared spectrum of the of III-121C.

Presence of conjugated double bond and carbonyl group was found by ultraviolet absorption spectroscopy and infrared absorption spectroscopy. The UV absorption spectrum and the IR absorption spectrum are shown in FIGS. 3 and 4, respectively.

Figure 5:
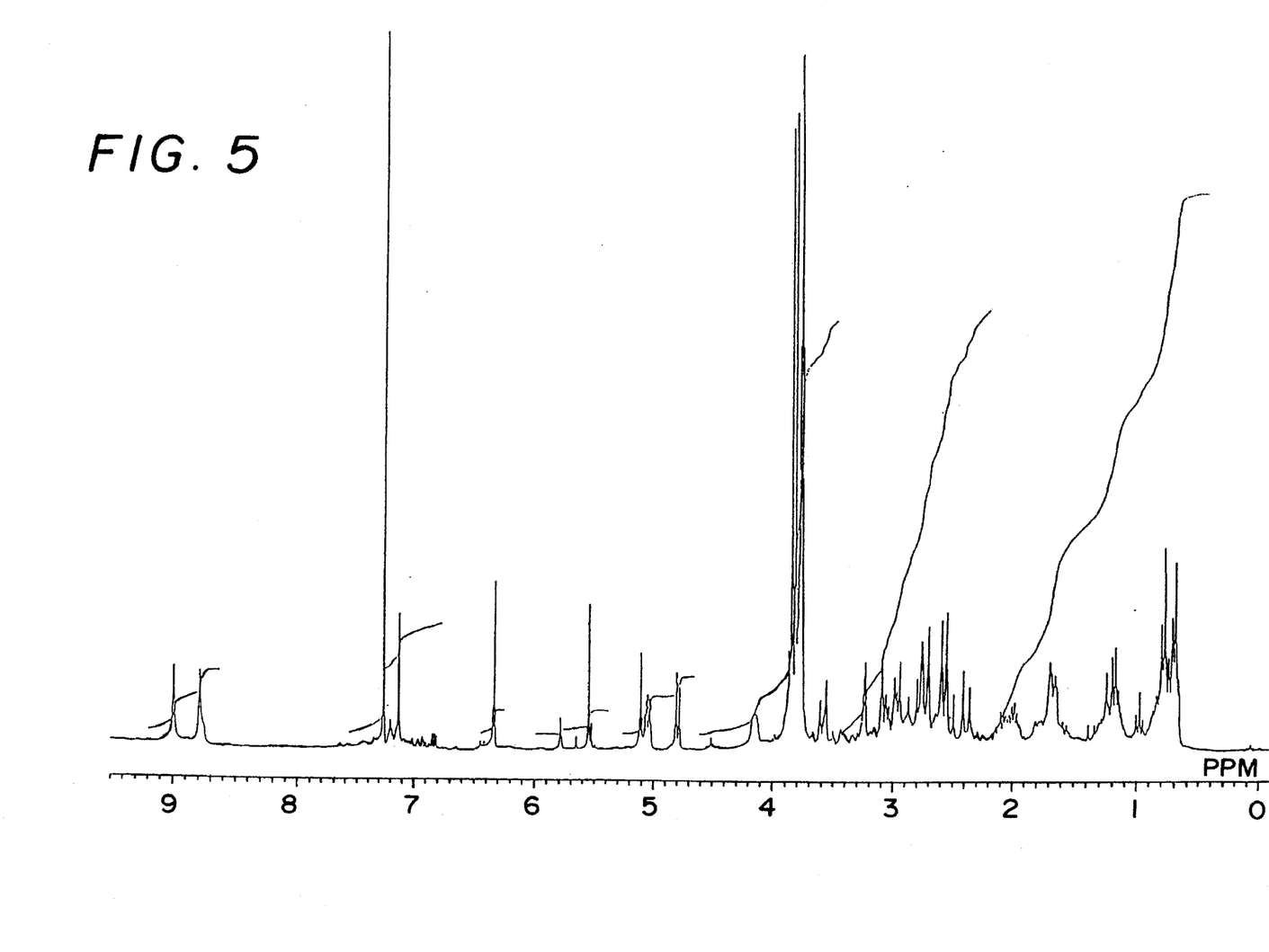
FIG. 5 is a $^1$H-NMR spectrum of III-121C.
Figure 6:
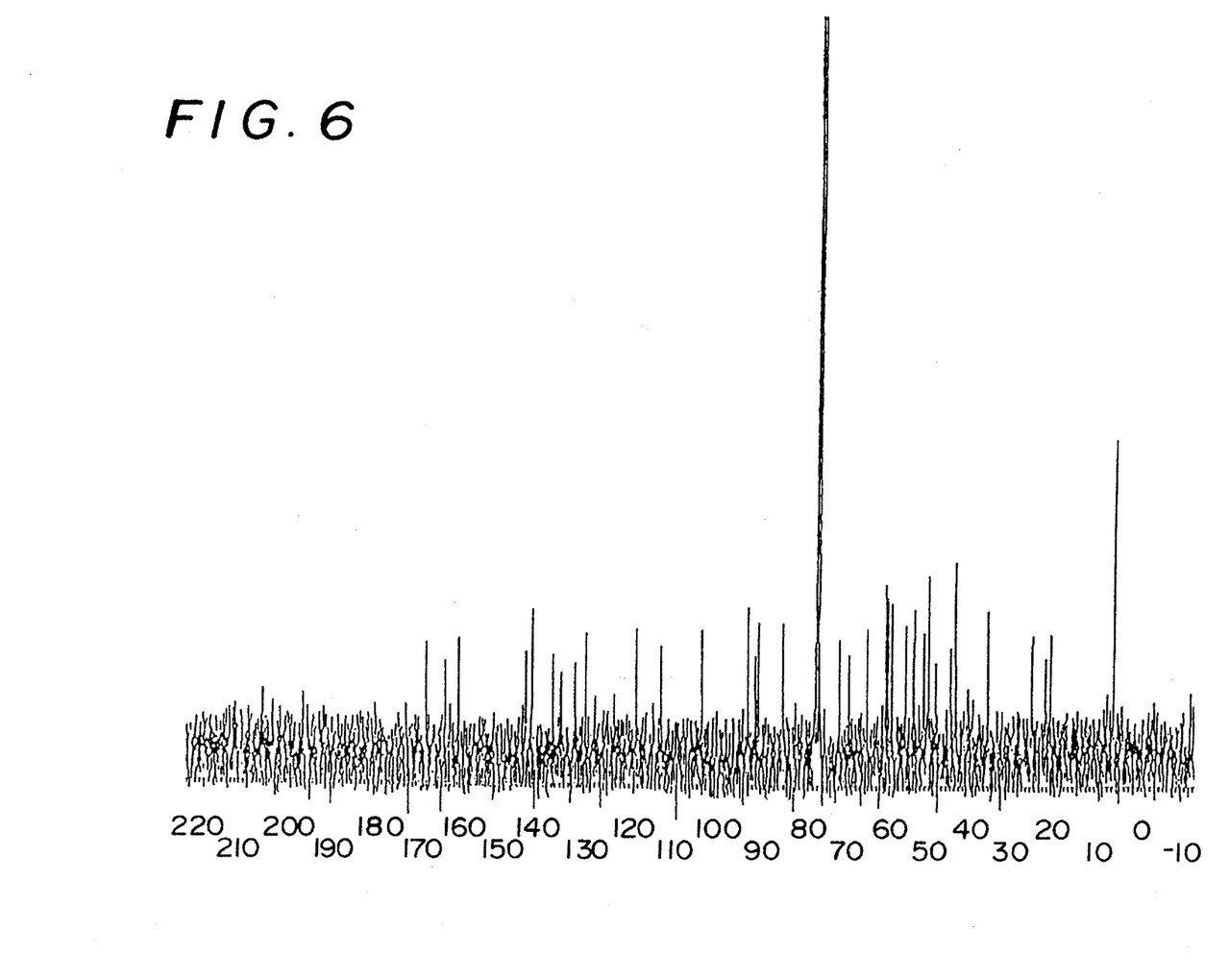
FIG. 6 is a $^{13}$C-NMR spectrum of III-121C.

III-121C exhibited $^1$H-NMR spectrum and $^{13}$C-NMR spectrum as shown in FIGS. 5 and 6, respectively.

III-121C was further characterized by various color reactions after subjecting III-121C to silica gel thin layer chromatography using 20:1 chloroform:methanol for the developer. In iodine reaction, yellow color development was observed on the TLC plate at the position corresponding to the R$_f$ of 0.56. In 2,4-Dichlorophenyl-hydrazine reaction, the position corresponding to the R$_f$ of 0.56 was observed to develop a red color, indicating the presence of carbonyl group. In Rydon-Smith reaction, no color development was observed to indicate the absence of peptide bond. In ninhydrine reaction, no color development was observed to indicate the absence of amino group. In α-naphthol-sulfuric acid reaction, no color development was observed to indicate the absence of sugar. In anisaldehyde reaction, no color development was observed to indicate the absence of sugar and steroid.

In view of the above findings, the compound isolated from *Ervatamia microphylla* Kerr. was concluded to have the structure represented by formula (I):

As described above, III-121C is a substance that has been found as a consequence of a screening for a substance that is capable of inhibiting the action of oncogene products.

Cell cultures that gave rise to immortal cell lines are used in cancer research as a model for in vivo animal cells. A typical such cell line that has been extensively used in cancer research is NIH 3T3 cells derived from a mouse. 3T3 cells undergo a dramatic change in its cell morphology and growth habits through their transition to malignancy by malignant transformation, for example, by oncogene. Moreover, such transformed 3T3 cells with changed growth properties can form tumors after they are injected into susceptible animals. Since the transformation of a cell line can be carried out entirely in culture, it has been widely studied as a model of cancer induction in animals. In addition to 3T3, there are many cell lines that are used in cancer research including NRK cell line used in the present invention.

One event that trigger the transformation is transcription of an oncogene, which is a gene whose product is involved either in transforming cells in culture on in inducing cancer in animals. The transformed cell lines are also extensively used in cancer research. Typical transformed cell lines include those used in the present invention, i.e., K-ras-NIH3T3, H-ras-NIH3T3, N-ras-NIH3T3, K-ras-NRK, K-ras$^{ts}$-NRK, and RSV$^{ts}$-NRK.

It is the protein products encoded by the oncogenes (often referred to as oncogene proteins, for short) that transform cells to malignancy by affecting the growth-control system of the cell. The ras and src oncogenes whose function are inhibited by III-121C in the present invention are derived from genes encoding proteins that are thought to act as intracellular transducers, proteins which transmit signals from a receptor to their cellular targets, G proteins being the best-understood transducers. It is then assumed that III-121C used in the present invention affects an oncogene protein (Ras protein and/or Src protein (protein-tyrosine kinase, PTK)), and as a result, alters the cell growth-control system to change cell morphology and growth habits in vitro and inhibit tumor growth in vivo.

From the results of the Examples described hereinafter, the compound represented by the formula (I) has at least one activity selected from the following activities from (a) to (g).

(a) An inhibition of inducing changes in cell morphology and growth habit toward cancer cells.

(b) An inhibition of the function of a protein which expresses an oncogene.

(c) An inhibition of the function of a Ras protein which expresses aras oncogene.

(d) An inhibition of an oncogene function through inhibiting the function of a product of the oncogene.

(e) An inhibition of cancer of a mammal.

(f) An inhibitory activity effective for the function of an oncogene but not effective for cell division.

(g) An inhibitory activity of inducing changes in cell morphology to cancer cells which express Ras protein or Src protein.

As described above, when III-121C is added to the cultured cell lines that has been transformed with ras or src oncogenes, the cell morphology and growth habits change to those of their normal counterparts. More illustratively, when III-121C is added to the cultured transformed cell lines, shapes of the cells undergo a significant change, and the cells cease to grow atop the other, and growth rate is reduced. The concentration ($IC_{50}$) of the III-121C required for 50% inhibition of the cancer cell propagation, which varies by the type of the cancer cell to which the III-121C is added, were determined to be in the range of approximately from 0.1 to 0.5, preferably from 0.2 to 0.5 µg/ml (Table 1).

TABLE 1

| Cell line | $IC_{50}$, µg/ml |
| --- | --- |
| K-ras$^{ts}$ NRK (33° C.) | 0.29 |
| K-ras$^{ts}$ NRK (39° C.) | 0.20 |
| K-ras NRK | 0.40 |
| NRK | 0.19 |
| K-ras-NIH 3T3 | 0.40 |
| H-ras-NIH 3T3 | 0.48 |
| N-ras-NIH 3T3 | 0.12 |
| NIH 3T3 | 0.47 |
| RSV NRK (33° C.) | 0.11 |
| RSV NRK (39° C.) | 0.11 |

As described above, III-121C is capable of inducing change in cell morphology and growth habits of cultured transformant cell lines by inhibiting the oncogene function through inhibition of the function of the oncogene products.

The cell growth inhibitory mechanism of III-121C was also investigated by comparing with the cell growth inhibition by conventional microtubule inhibitors such as vinblastin, vincristine, and colchicine. It was then revealed that the cancer cell growth inhibition of III-121C is caused by a mechanism quite different from such conventional microtubule inhibitors, and III-121C is not associated with the cell division inhibitory action as in the case of such conventional microtubule inhibitors.

In addition to the change in cell morphology and growth habits of cultured transformed cell culture, III-121C can also induce growth suppression of tumors in living mammals as will be demonstrated in the Examples.

III-121C also exhibits low acute toxicity as will be demonstrated in the Examples.

Therefore, III-121C can be used for treating a cancer wherein ras, src and other oncogenes are involved, and III-121C would constitute a favorable carcinostatic medicament by optionally combining with a suitable pharmaceutically acceptable carrier. Exemplary carriers include excipients such as natural and synthetic aluminum silicate, microcrystalline cellulose, talc, dextrin, starch and lactose; and diluents such as vegetable oil and propylene glycol. The carcinostatic agent may also contain other pharmaceutically acceptable additives such as stabilizers, coating agents, suspending agents, emulsifying agents, solution adjuvants, preservatives, buffering agents, sweetening agents, and the like which may be used either alone or in combination of two or more. Such carcinostatic agent may be formulated in any desired dosage forms such as powders, granules, tablets, capsules, and injections.

The thus formulated carcinostatic agent may be principally orally administered. The course of administration, however, is not limited. Adult daily dose may vary in accordance with the course of administration and the conditions of the patient. Typical non-limiting adult daily dose in the case of oral administration is from 0.1 to 100 mg/day/1 kg body weight.

*Ervatamia microphylla* Kerr. is a small tree of Apocynaceae that naturally grow in South East Asia, and is cultivated in some areas. When the stock plant is collected, it may be dried to facilitate transportation and storage either by sun or in an oven of up to 60° C. Use of the ground material for the extraction is preferred.

The solvent used for the extraction of *Ervatamia microphylla* may preferably be a nonpolar solvent, and use of a hydrocarbon solvent or a halogenated hydrocarbon solvent is most preferable. Exemplary hydrocarbon solvents include pentane, hexane, heptane, octane, benzene, toluene, and xylene, and use of hexane is most preferable. Exemplary halogenated hydrocarbon solvents include chloroform, methylene dichloride and methylene tetrachloride, and use of chloroform is most preferable. The extraction solvents are not limited to the above-mentioned solvents and any solvent capable of reliably extracting III-121C may be used for the extraction.

The amount of the solvent used for the extraction is not limited to any specific range, and the solvent of any desired amount that is capable of extracting III-121C may be used. Typical amount used for the extraction of III-121C from *Ervatamia microphylla* is in the range of from 500 to 1,500 ml per 100 g of dried ground leaves of *Ervatamia microphylla*. The temperature of extraction is not limited to any specific range, and the extraction may be carried out at any desired temperature that would enable a stable extraction of III-121C with no decomposition. Preferred extraction temperature is in the range of from room temperature to 60° C. The period of extraction may vary in accordance with the extraction temperature, and typical period of extraction in the case of an extraction at room temperature is from 2 to 20 hours. It should be noted that the extraction may be repeated twice or more depending on the rate of the extraction.

III-121C is purified from the thus obtained extract. The purification may be carried out, for example, by condensing the extract, and then subjecting the condensate to chromatography, which may preferably be column chromatography, gel filtration chromatography, high performance liquid chromatography, liquid-liquid countercurrent distribution chromatography, or thin layer chromatography. The purification may also be carried out by a combination of two or more above-mentioned chromatographic processes. When column chromatography is employed for the purification, Merck silicagel 60 (manufactured by Merck & Co., Inc.) may be used for the carrier, and 100:1 chloroform:methanol may be used for the eluting agent. When gel filtration chromatography is employed for the purification, Toyopearl HW-40 (manufactured by Toso K.K.) may be used for the carrier, and methanol may be used for the eluting agent. The carrier and the eluting agent used are not limited to the above-mentioned combinations.

The thus purified substance was characterized as described above, and it was then found that the substance had a chemical structure represented by formula (1).

The present invention is described in further detail by referring to the following Examples which by no means limit the scope of the present invention.

EXAMPLES

1. Extraction of Active Substance from *Ervatamia microphylla*

A 85 g portion of *Ervatamia microphylla* leaves that had been dried in an oven at 60° C. was ground, and placed in a 2 liter conical flask. To the flask was added 850 ml of chloroform, and the mixture was stirred at room temperature for 5 hours. The above-described extraction procedure was repeated 3 times in total, each time using the fresh solvent. The extracted solutions were combined, and the solvent chloroform was distilled off under a reduced pressure, and the resulting product was lyophilized to produce 10.5 g of brown powder. The thus obtained powder was used for the subsequent purification.

2. Purification of Active Substance from the Extract

To a small amount of chloroform was dissolved 1.34 g of the extract, and the resulting solution was charged in a column having packed therein 10 g of silica gel (Merck silicagel 60, manufactured by Merck). To the column was first added 100% chloroform to elute the impurities, and then, 100:1 chloroform:methanol was added and the eluate was fractionated into portions of about 10 ml. Each fraction was examined by thin layer chromatography (silica gel; 20:1 chloroform:methanol solvent; UV 330 nm), and fractions having an Rf of 0.56 with blue color were collected. The thus collected fractions were dried under a reduced pressure and the resulting product had a weight of 83.6 mg. The product was evaluated for its ability to induce a change in cell morphology, and the product was confirmed to have an activity of normalizing the cell morphology.

The thus obtained active substance was dissolved in a small amount of methanol. After removing the precipitates, the solution was charged in a column of Toyopearl HW-40 that had been equilibrated with methanol to thereby carry out the gel filtration chromatography. The column was eluted with 100% methanol and 3 ml fractions were collected. The thus collected fractions were analyzed by thin layer chromatography using 20:1 chloroform:methanol for the developer. The fractions exhibiting blue spots at an Rf of 0.56 were collected, and lyophilized under a reduced pressure. The resulting product had a weight of 18.8 mg. This substance is hereinafter referred to as III-121C. III-121C was evaluated for its degree of purification by thin layer chromatography, and the chromatogram exhibited single spot. This fraction was evaluated for its ability to induce a change in cell morphology, and it was confirmed to have an activity of normalizing the cell morphology.

3. Physical and Chemical Properties of the Purified Product

The thus purified III-121C was measured for its physical and chemical properties. III-121C was also evaluated by various spectral analysis. The results are described below.

1) Physical and chemical properties

III-121C is a light yellow powdery substance. Upon evaluation by thin layer chromatography on a silica gel (Merck 5715, manufactured by Merck) using developer systems, 20:1 chloroform:methanol, 1:2 hexane:ethyl acetate, and 2:1 toluene:acetone, it exhibited an Rf value of 0.56, 0.25 and 0.52, respectively. III-121C was soluble in chloroform, ethyl acetate and methanol, and hardly soluble in hexane. When III-121C was measured for its melting point, it was burnt black at a temperature in the range of from 206° to 210° C. and became decomposed.

2) Mass spectroscopic analysis

The results of FAB mass spectroscopic measurement are shown in FIGS. 1 and 2. As shown in FIG. 1, the positive spectrum had a characteristic peak at 795.4 m/z, and as shown in FIG. 2, the negative spectrum had a characteristic peak at 793.3 m/z. The molecular weight was then determined to be 794.

3) UV spectroscopic analysis

The measurements of UV absorption spectrum, $\lambda_{max}$ (E 1%/1 cm), are shown in FIG. 3. Under neutral conditions (MeOH), the absorption was found at 330 nm (224). Under acidic conditions (HCl/MeOH), the absorption was found at 330 nm (203) and 245 nm (195). Under basic conditions (NaOH/MeOH), the absorption was found at 339 nm (182) and 254 nm (180). The pH change did not result in any significant shift of the peaks.

4) IR spectroscopic analysis

The results of IR spectroscopic measurement are shown in FIG. 4. An absorption which is estimated to correspond to methylene group is found at 2930 $cm^{-1}$. Presence of carbonyl group is indicated by the absorption at 1676 $cm^{-1}$, and presence of a conjugated double bond is indicated by the absorption at 1610 $cm^{-1}$.

5) $^1$H-NMR spectroscopic analysis

The results of $^1$H-NMR spectroscopic measurement are shown in FIG. 5. The peak at 0.75 ppm is estimated to correspond to methyl group, and the peaks at 2.0 to 3.7 ppm are estimated to correspond to methylene group. The peak at 3.8 ppm is estimated to correspond to methoxy group. When III-121C was substituted with deuterium, the singlet at 5.1 ppm disappeared to indicate the presence of replaceable proton.

6) $^{13}$C-NMR spectroscopic analysis

The results of $^{13}$C-NMR spectroscopic measurement are shown in FIG. 6. The peak at 6.2 ppm is estimated to correspond to methyl group, and the peaks at 40 to 60 ppm are estimated to correspond to methylene group. The peaks at 100 to 140 ppm are estimated to correspond to carbon atoms having double bonds.

7) Color reactions a. Iodine reaction

The purified sample of III-121C was spotted on silica gel TLC plate (Merck 5715, manufactured by Merck), and developed with 20:1 chloroform:methanol. After confirming that the solvent had been fully removed, the TLC plate was placed in a sealed container filled with gaseous iodine for about 5 minutes. After 5 minutes, yellow color development was observed on the TLC plate at the position corresponding to an $R_f$ of 0.56 where the purified sample had been spotted. Presence of an unsaturated double bond in the purified product was thus indicated.

b. 2,4-Dinitrophenyl-hydrazine reaction 2,4-Dinitrophenyl-hydrazine (0.1 mg/100 ml 2N HCl) was sprayed onto the TLC plate wherein the III-121C sample had been developed by repeating the procedure of the above a, and the plate was heated on a hot plate. After several minutes, red color development was observed at the position corresponding to an $R_f$ of 0.56. Presence of carbonyl group in the purified product was then indicated.

c. Rydon-Smith reaction

Onto the TLC plate wherein the III-121C sample had been developed by repeating the procedure of the above a was sprayed 1% sodium hypochlorite solution, and then, 100% ethanol, and the plate was fully dried. Onto the thus dried plate was then sprayed a mixed solution of 1% soluble starch and 1% potassium iodide, and the plate was observed for color development. No color development could be observed to indicate the absence of peptide bond.

d. Ninhydrin reaction

Onto the TLC plate wherein the III-121C sample had been developed by repeating the procedure of the above a was sprayed ninhydrin solution (a mixed solution of ninhydrin 3 mg/1000 ml n-BuOH and 3 ml of $CH_3COOH$) and the plate was heated on a hot plate to observe the color development. No color development could be observed to indicate the absence of amino group.

e. α-naphthol reaction

Onto the TLC plate wherein the III-121C sample had been developed by repeating the procedure of the above a was sprayed α-naphthol solution (a mixed solution of 10.5 ml of 15% α-naphthol/EtOH, 6.5 ml of $H_2SO_4$, 40.5 ml of EtOH, and 4.0 ml of $H_2O$) and the plate was heated on a hot plate to observe the color development. No color development could be observed to indicate the absence of sugar.

f. Anisaldehyde reaction

Onto the TLC plate wherein the III-121C sample had been developed by repeating the procedure of the above a was sprayed anisaldehyde solution (a mixed solution of p-anisaldehyde 0.5 ml/50 ml $CH_3COOH$ and 1 ml of $H_2SO_4$) and the plate was heated on a hot plate to observe the color development. No color development could be observed to indicate the absence of sugar and steroid.

4. Activity of III-121C to Induce Changes in Cell Morphology

A cell line that had been established from rat kidney cells and transformed with temperature sensitive Kirsten sarcoma virus, K-$ras^{ts}$-NRK (National Institute of Health, U.S.) and a cell line that had been established from rat kidney cells and transformed with temperature sensitive Rous sarcoma virus, $RSV^{ts}$-NRK (Tokyo University, Medical Science Institute, Japan) were incubated at 33° C., which is the temperature at which the cultured cells would exhibit cancer cell morphology, and at 39° C., which is the temperature at which the cultured cells would exhibit normal cell morphology, in a culture medium comprising Dulbecco Modified Eagle's Medium (DMEM, manufacture by Nissui Pharmaceutical K.K.) containing 5% bovine serum albumin (Gibco/BRL) having added thereto 0.6 g/l glutamine, 0.2 g/l kanamycin, and 2.25 g/l $NaHCO_3$ in an incubator of 5% $CO_2$. Normal rat kidney cell, NRK-49 (Dainihon Pharmaceutical K.K.) and normal mouse cell, NIH 3T3 (JCRB Cell Bank); and K-ras NIH 3T3, H-ras NIH 3T3, and N-ras NIH 3T3 (Tokyo University, Medical Science Institute, Japan) which are cell lines that have been transformed with Kirsten sarcoma virus, Harvey sarcoma virus, and neuroblastoma virus, respectively, were incubated at 37° C. in the similar manner.

The effect of the III-121C on various types of cultured cells was evaluated by inoculating each type of cells in wells of 24 wells plastic plate (Costar 3524, manufactured by Costar) at $3\times10^4$ cells/1 ml medium/well; incubating the plate in an incubator of 5% $CO_2$ for one day; and adding the III-121C sample to the cell cultures to observe the cell morphology for another two days.

(1) K-$ras^{ts}$-NRK cells

The cells of K-$ras^{ts}$-NRK incubated at 33° C. have thin projections or processes and the cells grow one atop the other to exhibit the cancerous cell morphology. In contrast, the cells of K-$ras^{ts}$-NRK incubated at 39° C. are flat and free from projections or processes, and do not grow one atop the other to exhibit normal cell morphology.

When 0.3 μg/ml of III-121. C was added to the culture of K-$ras^{ts}$-NRK that had been incubated at 33° C. and the incubation was continued at the same temperature for another 2 days, the cells changed their morphology and growth habits to those of normal cells, and the cells no longer grew one atop the other and were rather flat and free from projections or processes. When III-121C was added to the culture of K-$ras^{ts}$-NRK cells that had been incubated at 39° C. and the incubation was continued at the same temperature for another 2 days, the cell morphology and growth habits were the same as the K-$ras^{ts}$-NRK cells that had been incubated in the absence of III-121C.

(2) K-ras-NRK cells

K-ras-NRK is a transformed cell line, and the cells appear round with its central portion raised. When 0.3 μg/ml of III-121C was added to the K-ras-NRK cell culture and the cell culture was incubated for another 2 days, the cells changed their morphology and growth habits to those of normal cells, and became flat with an increased area of contact.

(3) K,H, and N-ras-NIH 3T3 cells

K-ras-NIH 3T3 and H-ras-NIH 3T3 are transformed cell lines, and the cells are elongated with projections or processes on their surface, and grow atop the other. N-ras-NIH 3T3 cells are also elongated and their projections or processes are even longer.

When 0.3 μg/ml of III-121C was added to the cultured cells and the cell cultures were incubated for another 2 days, the cells changed their morphology and growth habits to those of normal NIH 3T3 cells, and became flat with an increased area of contact.

(4) $RSV^{ts}$-NRK cells $RSV^{ts}$-NRK is a cell line that had been transformed with an src oncogene, and is temperature sensitive as in the case of K-$ras^{ts}$-NRK. The cells of $RSV^{ts}$-NRK incubated at 33° C. exhibit cancer cell morphology of an elongated diamond shape, while the cells of $RSV^{ts}$-NRK incubated at 39° C. exhibit normal flat cell morphology with a larger area of contact.

When 0.3 μg/ml of III-121C was added to the cultured cells that have been respectively incubated at 33° C. and 39° C., and the incubation was continued for another 2 days, the cells of both temperatures changed their cell morphology to have a rounded appearance similar to the morphology of the normal NRK-49 cells.

5. Effect of III-121C on Production of Actin Filaments in Various Types of Cells A cover glass with a diameter of 18 mm (manufactured by Matsunami Glass Industry K.K.) that had been washed with 100% ethanol, dried, and sterilized was placed in wells of 12 wells plastic plate, and the cells were inoculated in the wells at $3.0\times10^4$/DMEM 1 ml/well. The plate was incubated in an incubator of 5% $CO_2$ for 1 day. To the thus incubated cell culture was added 1 μg/ml of III-121C, and the incubation was continued for another one day. The cell culture was then fixed with paraformaldehyde. The fixed cell culture was reacted with rhodamine pharoidine reagent (Molecular Probe Inc.) to examine the cell morphology by fluorescence microscope with G filter (excitation, 546 nm).

The cells of K-ras$^{ts}$-NRK, K-ras-NRK, K-ras-NIH 3T3, and H-ras-NIH 3T3 were examined, and the cells were observed to have the morphology of normal cells with longitudinally extending linear actin filaments.

6. Propagation Inhibitory Effect of III-121C on Various Types of Cells

Figure 7:
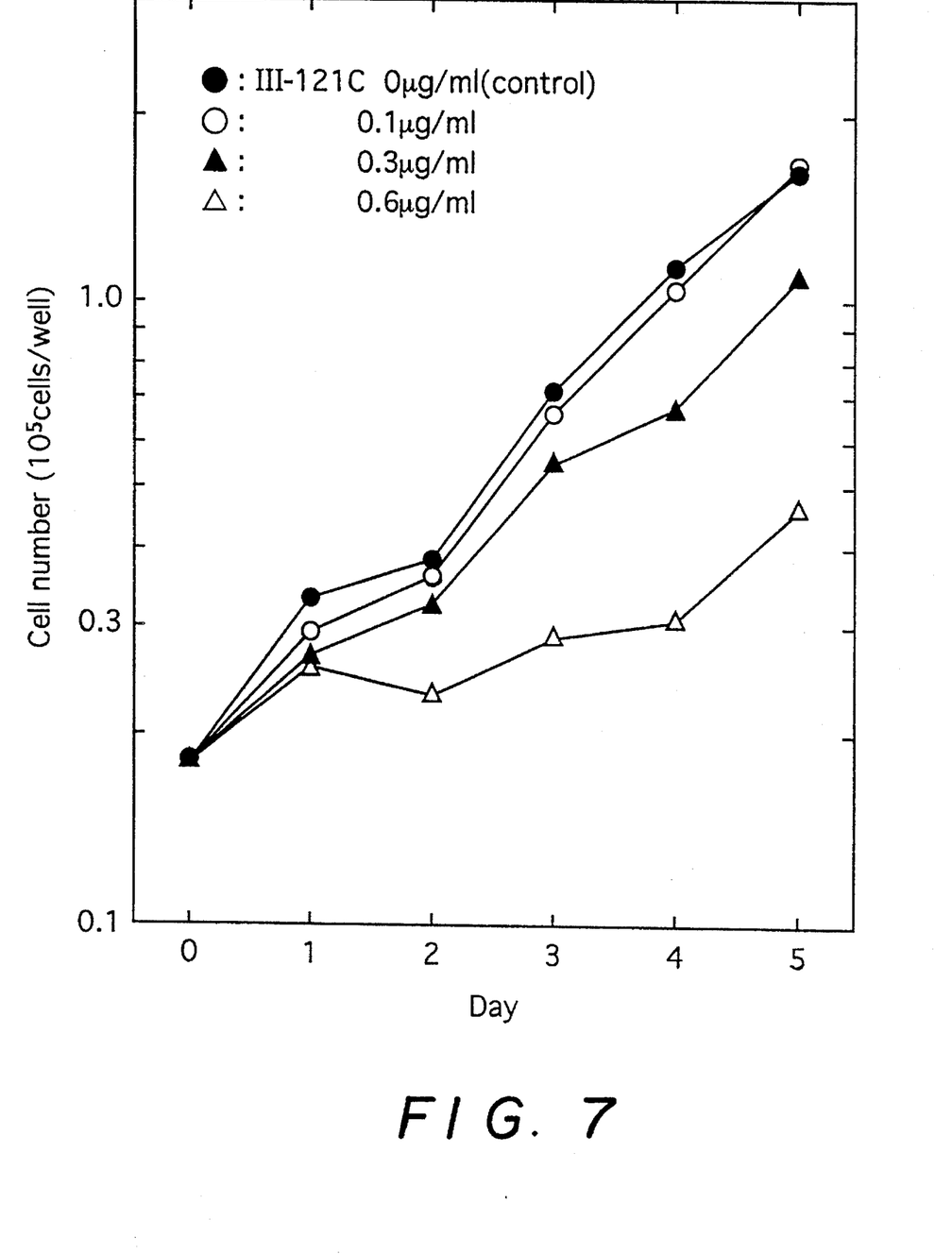
FIG. 7 is a cell growth curve for K-ras$^{ts}$-NRK wherein inhibition of the cell propagation by III–121C in concentration dependent manner is demonstrated.

Cells of K-ras$^{ts}$-NRK were inoculated in wells of 24 wells plastic plate (Costar 3524, manufactured by Costar) at $1.0 \times 10^4$/DMEM 1 ml/well, and the plate was incubated in an incubator of 5% $CO_2$ at 33° C. for one day. III-121C was added to the thus incubated cells to different concentrations and the incubation was continued. After predetermined periods, the medium was removed of the cell culture, and cells were peeled off the wall of the well by using trypsin. DMEM was added to the well to uniformly suspend the cells, and the cell concentration in the suspension was measured with Coulter counter (ZM type manufactured by Coulter Electronics) to obtain the results shown in FIG. 7. As shown in FIG. 7, III-121C inhibited the cell propagation in concentration dependent manner.

Next, cells of different types were inoculated in wells of 12 wells plastic plate (Costar 3521, manufactured by Costar) at $2.0 \times 10^4$/DMEM 1 ml/well, and the plate was incubated in an incubator of 5% $CO_2$ for one day. III-121C was added to the thus incubated cells to different concentrations and incubation was continued for another 3 days. The number of cells was measured by repeating the above-described procedure to determine the concentration ($IC_{50}$) of the III-121C required to inhibit the cell propagation to 50%. The results are shown in Table 1.

7. Acute Toxicity of III-121C

Toxicity ($LD_{50}$) on mouse of III-121C upon intravenous injection was measured. The results are shown below.

| | |
|---|---|
| III-121C | 24.3 mg/kg |
| vincristine sulfate | 2.5 mg/kg |
| vindecine sulfate | 9.1 mg/kg |
| vinblastine sulfate | 15.2 mg/kg |

The results indicate the weaker toxicity on mice of III-121C compared to conventional alkaloid carcinostatics of plant origin.

8. Experimental Administration of III-121C to Mouse

To 4 groups of nude mice (each group comprising 6 individuals) were subcutaneously inoculated $1 \times 10^6$ cells of K-ras-NRK on their back. Formation of a small tumor was recognized after 4 days from the inoculation, and intraperitoneal administration of III-121C at different doses was started on this day (day 0). III-121C was additionally administered after two days and four days from the start of the administration to measure the volume of the tumor. No III-121C was administered to the mice of the control group. The results are depicted in FIG. 8.

Figure 8:
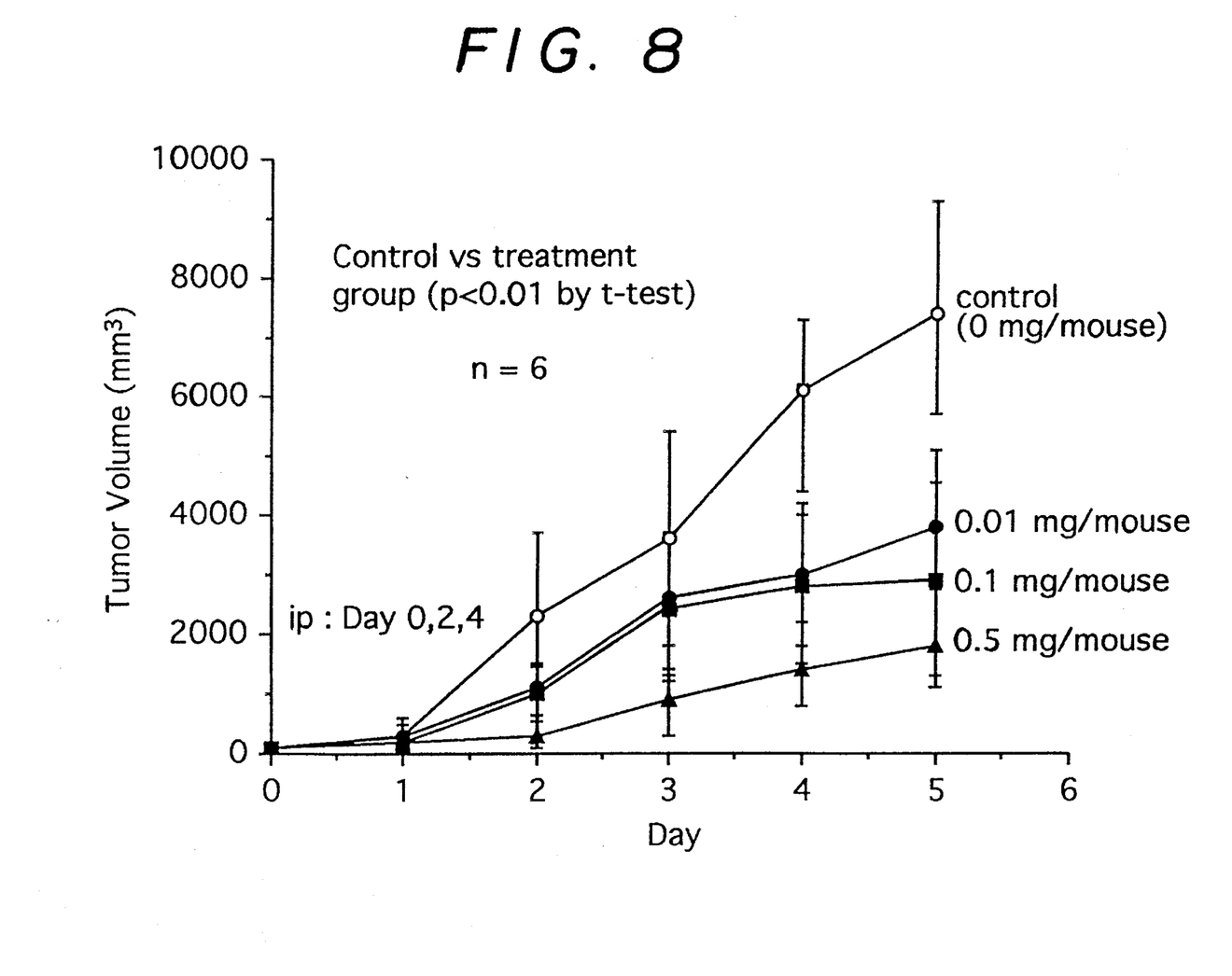
FIG. 8 diagrammatically illustrates growth suppression by III-121C of the tumor generated by inoculating K-ras-NRK cells in nude mice.

As shown in FIG. 8, the growth of the tumor was inhibited in a dose dependent manner.

9. Action Mechanism of III-121C -1

Figure 9A:
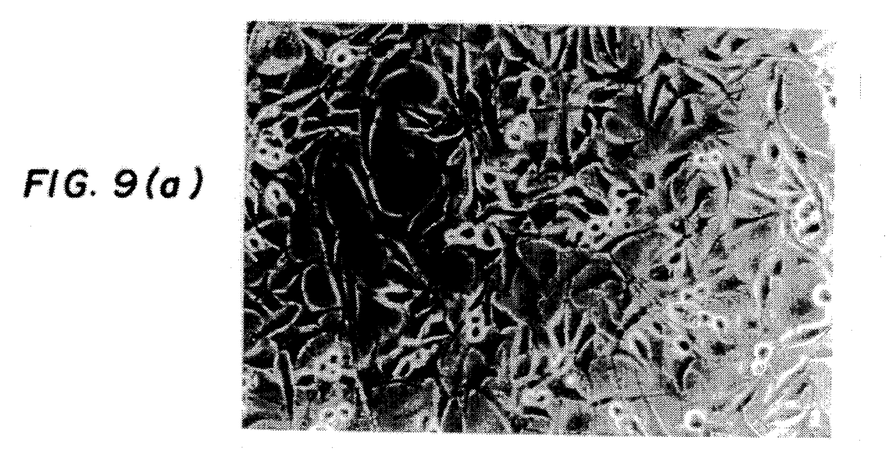
FIG. 9(a) is a photomicrograph of K-ras$^{ts}$-NRK cell culture that has been incubated at 33° C. (control).
Figure 9B:
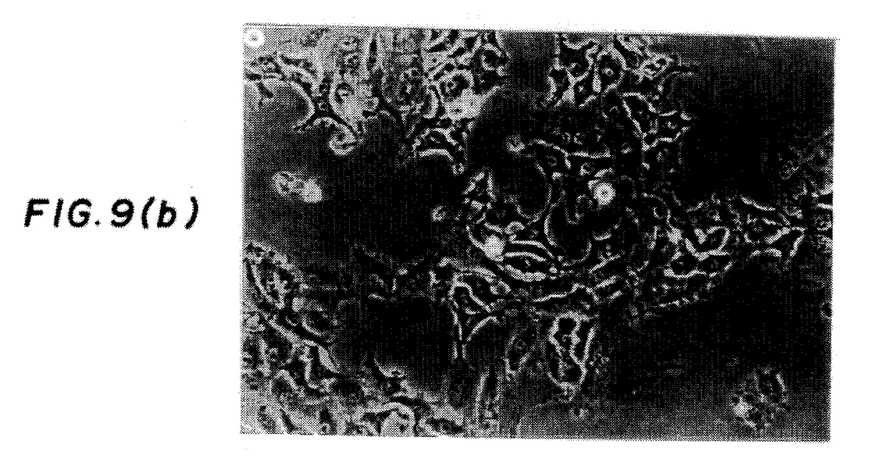
FIG. 9(b) is a photomicrograph of K-ras$^{ts}$-NRK cell culture incubated at 33° C. after one day from the addition of 1 μg/ml of III-121C.
Figure 9C:
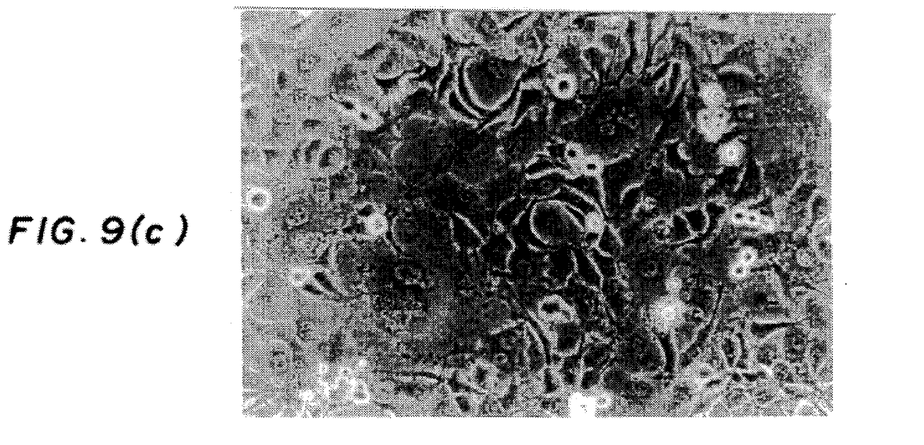
FIG. 9(c) is a photomicrograph of K-ras$^{ts}$-NRK cell culture incubated at 33° C. after two days from the addition of 1 μg/ml of III-121C.

To the cells of K-ras$^{ts}$-NRK that had been incubated at 33° C. was added 1 μg/ml of III-121C, and the incubation was continued at the same temperature. Before the addition of the III-121C, the cells grew atop the other and had projections or processes on their surface (FIG. 9(a)). After one day from the addition of the III-121C, the cells no longer grew atop the other and became flat (FIG. 9(b)). After two days, such change in the cell morphology and growth habits were even more significant (FIG. 9(c)).

Figure 10A:
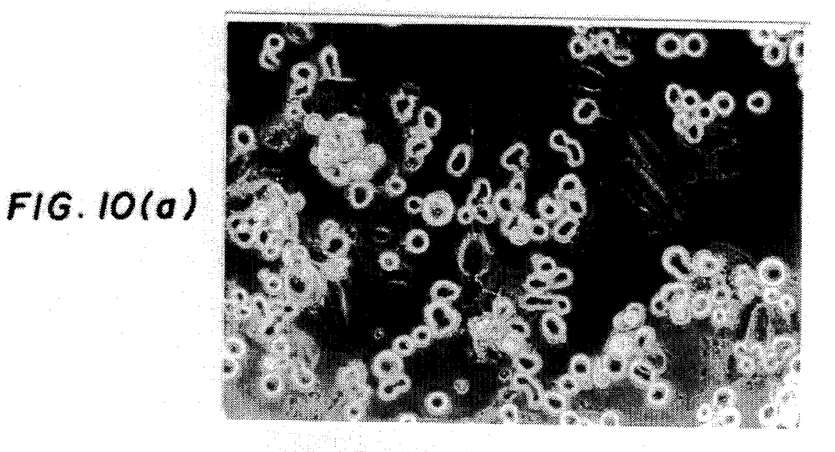
FIG. 10(a) is a photomicrograph of K-ras$^{ts}$-NRK cell culture incubated at 33° C. after one day from the addition of 0.1 μg/ml of vinblastine.
Figure 10B:
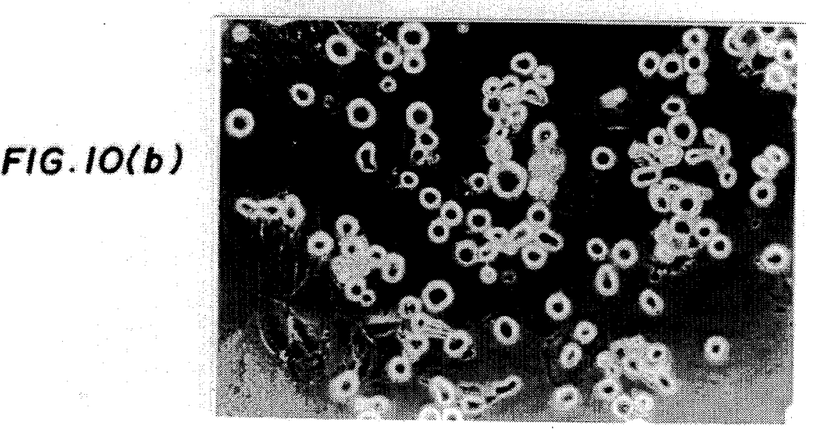
FIG. 10(b) is a photomicrograph of K-ras$^{ts}$-NRK cell culture incubated at 33° C. after one day from the addition of 0.1 μg/ml of vincristine.
Figure 10C:
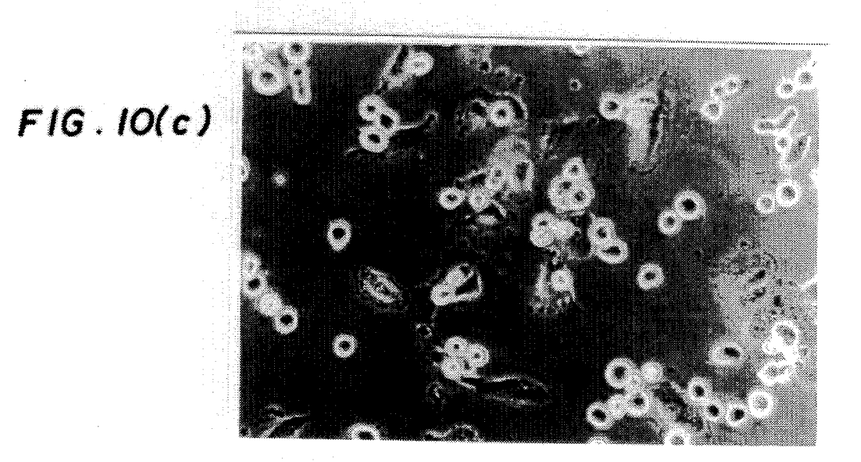
FIG. 10(c) is a photomicrograph of K-ras$^{ts}$-NRK cell culture incubated at 33° C. after one day from the addition of 0.1 μg/ml of colchicine.

The procedure as described above was repeated by replacing the III-121C with 0.1 μg/ml of vinblastine, 0.1 μg/ml of vincristine and 0.1 μg/ml of colchicine, which are known as microtubule formation inhibitors. After one day from the addition of such reagent, a significant increase in the number of circular or elongated cells that are in their M phase of the cell cycle was observed (FIG. 10(a), (b) and (c)).

The results indicate that III-121C has an anti-ras activity while it is free from the cell division inhibitory activity.

10. Action Mechanism of III-121C -2

To the cells of K-ras-NRK in their propagation was added either one of III-121C and vinblastine. No reagent was added to the control cells. After 24 hours from the addition, the cells were fractionated with a cell sorter to examine the DNA quantity in relation to the number of the cells. The results are shown in FIGS. 11(a) to 11(d).

Figure 11A:
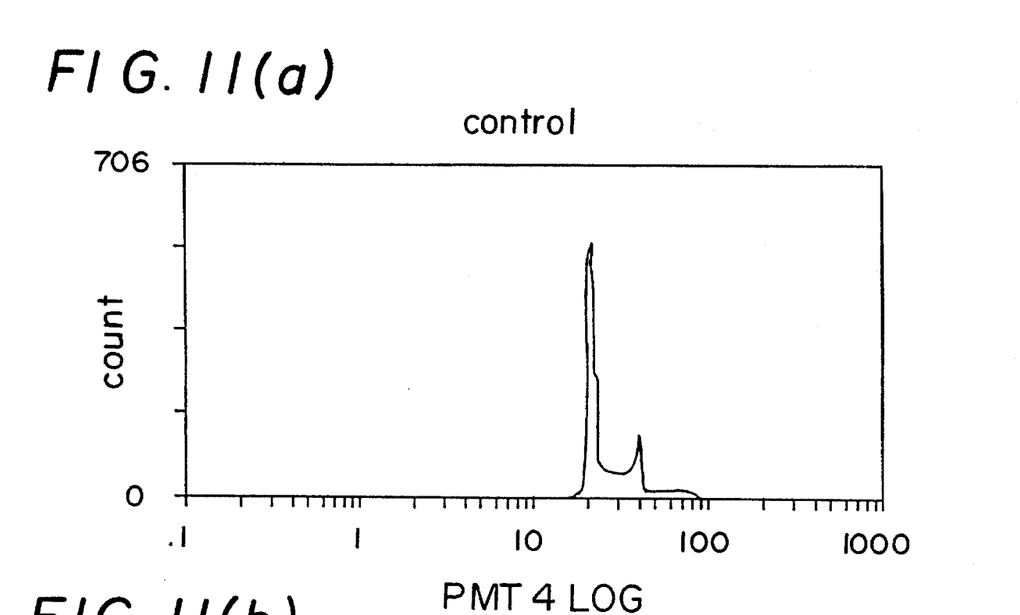
FIGS. 11(a) to (d) are graphs showing the results of flow-cytometric analysis wherein the number of cells is depicted in relation to their DNA content, upon addition of no reagent (FIG. 11(a)), 0.3 μg/ml of III-121C (FIG. 11(b)), 1 μg/ml of III-121C (FIG. 11(c)), and 0.1 μg/ml of vinblastine (FIG. 11(d)) to the K-ras NRK cell culture.
Figure 11B:
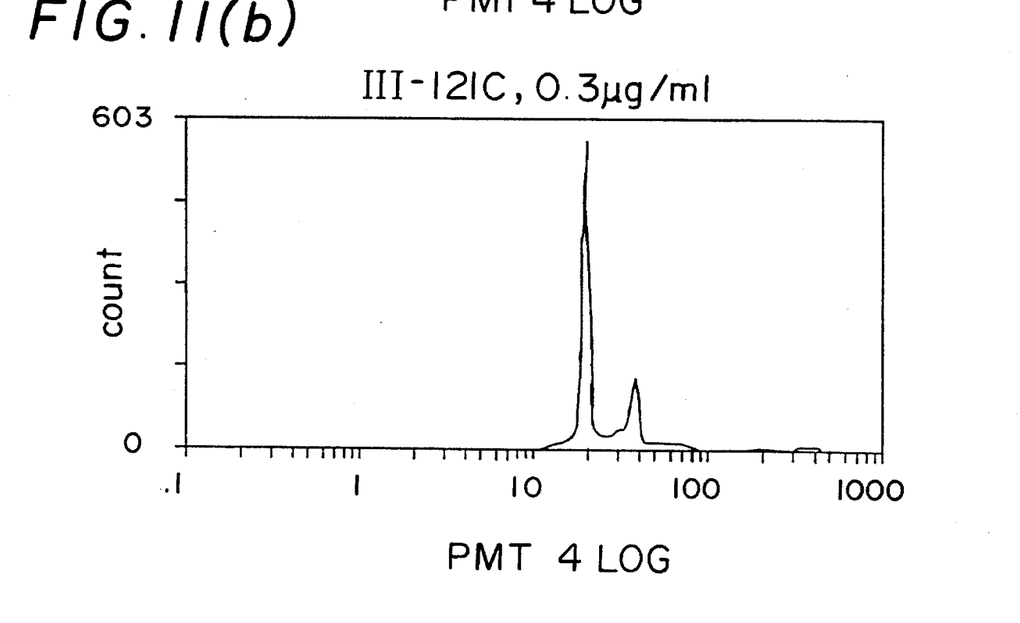
Figure 11C:
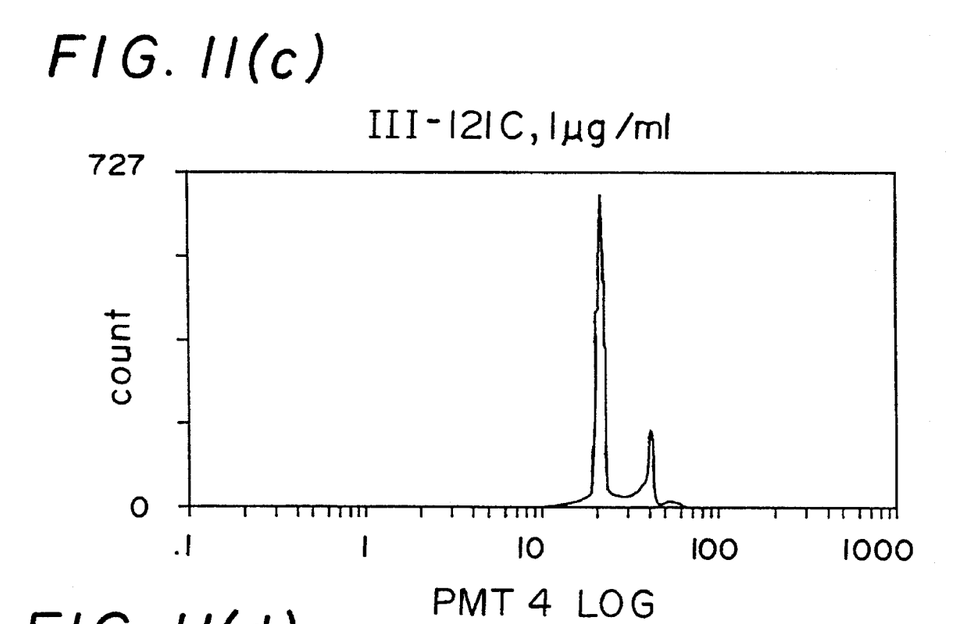
Figure 11D:
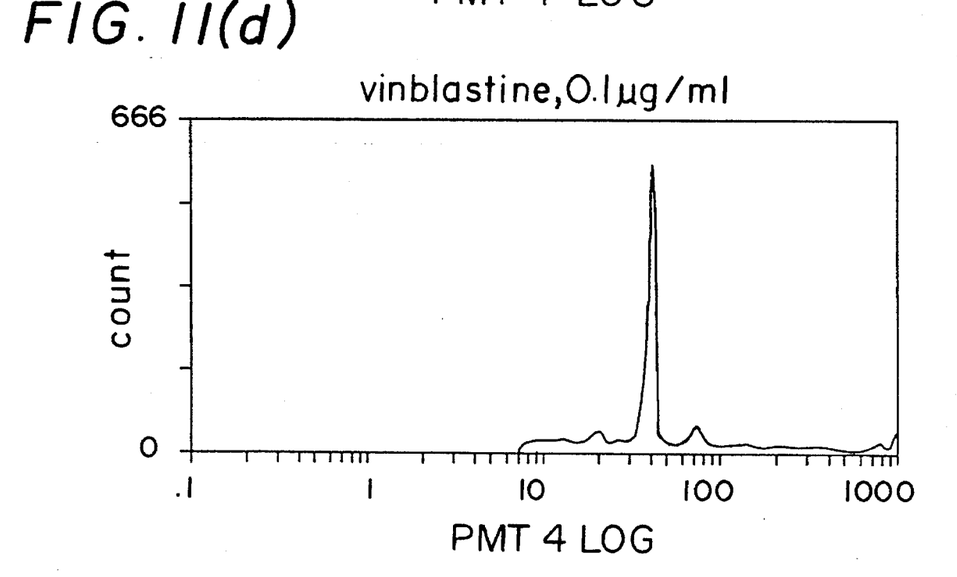

When vinblastine was added to the propagating cells, an increase in the number of cells having a relatively large quantity of DNA was observed (FIG. 11(d)) to clearly indicate the inhibition of $G_2$/M phase in the cell cycle. In contrast, when III-121C was added to the cells, distribution of the DNA quantity in the cells was identical with that of the control cells. Absence of the cell division inhibitory activity of III-121C was thus indicated.

As described above, III-121C has an action mechanism that is quite different from the conventional alkaloid carcinostatics such as vinblastine.

EFFECTS OF THE INVENTION

As described above, the compound of formula (1) used in the present invention that has been extracted from a tropical plant, *Ervatamia microphylla* has an activity of inducing a change in cell morphology and growth habits in cultured transformed cell lines, as well as an activity to reduce the size of tumor in a mammal. In addition, the mechanism of its action was different from conventional microtubule inhibitors such as vinblastine, vincristine, and colchicine. Therefore, the compound of formula (1) should be quite useful in treating the cancer of mammals.

We claim:

1. A pharmaceutical composition suitable for treatment of cancer sensitive to a compound represented by general formula (I) below which composition contains an effective amount of a compound represented by general formula (I):

in combination with a pharmaceutically acceptable carrier which is in the form of a dosage form selected from the group consisting of powder, granules, tablets, capsules and injectable compositions.

2. The pharmaceutical composition of claim 1 wherein the pharmaceutically acceptable carrier is selected from the group consisting of natural and synthetic aluminum silicate, microcrystalline cellulose, talc, dextrin, starch, lactose, vegetable oil, and propylene glycol.

3. The pharmaceutical composition of claim 1 which further contains an additive selected from the group consisting of stabilizers, coating agents, adjuvants, preservatives, buffering agents, and sweetening agents.

4. A method of treating a subject having a cancer sensitive to treatment with a compound of general formula (I) below by administration of an effective amount of a compound represented by formula (I):

5. The method of claim 4 wherein said cancer is caused by an oncogene.

6. The method of claim 5 wherein said oncogene is selected from the group consisting of ras and src oncogenes.

7. The method of claim 6 wherein the ras oncogenes are selected from the group consisting of k-ras, H-ras and N-ras.

8. The method of claim 4 wherein said compound is administered orally.

9. The method of claim 8 wherein the orally administered dosage to said subject ranges from about 0.1 to 100 mg/day/kg of body weight.

10. The method of claim 4 wherein said compound is mixed with a pharmaceutically acceptable carrier.

11. The method of claim 10 wherein said carrier is selected from the group consisting of natural and synthetic aluminum silicates, microcrystalline cellulose, talc, dextrin, starch, lactose, vegetable oil and propylene glycol.

12. The method of claim 4 wherein the compound is administered in a dosage selected from the group consisting of powders, granules, tablets, capsules and an injectable composition.

13. The method of claim 12 wherein the dosage form contains an additive selected from the group consisting of stabilizers, coating agents, adjuvants, preservatives, buffering agents and sweetening agents.

* * * * *